(12) United States Patent
Mankos et al.

(10) Patent No.: US 6,803,571 B1
(45) Date of Patent: Oct. 12, 2004

(54) METHOD AND APPARATUS FOR DUAL-ENERGY E-BEAM INSPECTOR

(75) Inventors: Marian Mankos, San Francisco, CA (US); David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/607,226

(22) Filed: Jun. 26, 2003

(51) Int. Cl.$^7$ .................. H01J 37/26; G01N 23/225

(52) U.S. Cl. .................. 250/310; 250/307; 250/305

(58) Field of Search ................... 250/310, 307, 250/305

(56) References Cited

U.S. PATENT DOCUMENTS

| | | | |
|---|---|---|---|
| 4,564,758 A | * | 1/1986 | Slodzian et al. ............ 250/310 |
| 6,586,733 B1 | * | 7/2003 | Veneklasen et al. ........ 250/310 |
| 6,610,980 B2 | * | 8/2003 | Veneklasen et al. ........ 250/310 |

FOREIGN PATENT DOCUMENTS

WO    WO 01/88514 A1    11/2001

OTHER PUBLICATIONS

L. Veneklasen, "The continuing development of the low energy electron microscope for characterizing surfaces", Dec. 1992, pp. 5513–5532, vol. 63, No. 12, Rev. Sci. Institute of Physics.

J. Chmelik et al. "Comparing cathode lens configuration for low energy electron microscopy", 1989, pp. 155–160, vol. 83, No. 5, Optik.

* cited by examiner

*Primary Examiner*—Jack I. Berman
(74) *Attorney, Agent, or Firm*—Okamoto & Benedicto LLP

(57) ABSTRACT

In accordance with one embodiment, the disclosure pertains to an apparatus for inspection of substrates. The apparatus includes at least a dual-energy e-beam source, an energy-dependent dispersive device, a beam separator, and an objective lens. The dual-energy e-beam source is configured to generate both a higher-energy e-beam component and a lower-energy e-beam component. Said two components exit the dual-energy e-source co-axially. The energy-dispersive device is configured to introduce dispersion between the two components. The components exit the dispersive device at different angles of trajectory. The beam separator is configured to receive the two dispersed components and substantially cancel the dispersion previously introduced by the dispersive device. As a result, the two components are rejoined in trajectory. Finally, the objective lens configured to focus said two rejoined components onto an area of the substrate.

23 Claims, 4 Drawing Sheets

400

METHOD AND APPARATUS FOR DUAL-ENERGY E-BEAM INSPECTOR

BACKGROUND OF THE INVENTION

1. Field of the Invention

The present invention relates generally to electron beam (e-beam) apparatus and e-beam inspection methods.

2. Description of the Background Art

Most conventional wafer and mask inspection systems use light optical images. Scanning electron beam microscopes (SEMs) have also been developed for inspection and critical dimension (CD) measurement. These SEM instruments scan a very small beam over the surface, and record the re-emitted secondary electrons in a single detector. Image acquisition tends to be slower for SEMs than for direct imaging light optical instruments because only one image element (pixel) at a time is recorded.

A low energy emission microscope (LEEM) is a direct imaging (as opposed to scanning) electron microscope. A conventional LEEM uses a single illumination beam which is accelerated typically to about 10 to 30 keV in an electron gun. The single beam passes through a separator magnet that bends the beam into the axis of the objective lens. An image of the gun crossover is transferred to the back focal (diffraction) plane of the objective lens, forming a parallel flood beam that uniformly illuminates the substrate. The substrate is electrically floated at approximately the same voltage as the cathode of the electron gun, so that illuminating electrons are decelerated in the objective lens, striking the substrate at energies typically between 0 to about 1000 eV. Some examples of prior art LEEM systems are described in the review paper: "The continuing development of the low energy electron microscope for characterizing surfaces," L. Veneklasen, Rev. Sci. Inst. 63(12) p. 5513 (December 1992) and its references.

Insulating surfaces are generally not a problem for light optical inspection because the scattering and reflection of light is insensitive to electrostatic surface charge. Unfortunately, surface charging effects can pose a difficulty for electron beam imaging of insulating surfaces (whether scanned or direct imaging). The rate that a given pixel element charges depends upon the difference between electron flux arriving at and leaving each pixel. The high current densities required for imaging at inspection rates imply a likely high rate of charging if the electron flux leaving the surface is not balanced by that entering. Thus, the surface voltage can quickly reach levels detrimental to imaging or even, in some instances, detrimental to sample integrity. Effective means for controlling local surface charging are therefore desirable if e-beam instruments are to be used for inspection of wafers, masks and other non-conductive substrates.

SUMMARY

In accordance with one embodiment, the invention relates to an apparatus for inspection of substrates. The apparatus includes at least a dual-energy e-beam source, an energy-dependent dispersive device, a beam separator, and an objective lens. The dual-energy e-beam source is configured to generate both a higher-energy e-beam component and a lower-energy e-beam component. Said two components exit the dual-energy e-source co-axially. The energy-dispersive device is configured to introduce dispersion between the two components. The components exit the dispersive device at different angles of trajectory. The beam separator is configured to receive the two dispersed components and substantially cancel the dispersion previously introduced by the dispersive device. As a result, the two components are rejoined in trajectory. Finally, the objective lens configured to focus said two rejoined components onto an area of the substrate.

In accordance with another embodiment, the invention relates to a method for in-line inspection of a substrate. A dual-energy e-beam including a higher-energy e-beam component and a lower-energy e-beam component. Dispersion is introduced between the two e-beam components so that the two e-beam components have different angles of trajectory. Subsequently, the dispersion is substantially canceled so that said two e-beam components are rejoined in trajectory. The two rejoined e-beam components are then focused onto an area of the substrate.

DETAILED DESCRIPTION

Figure 1:
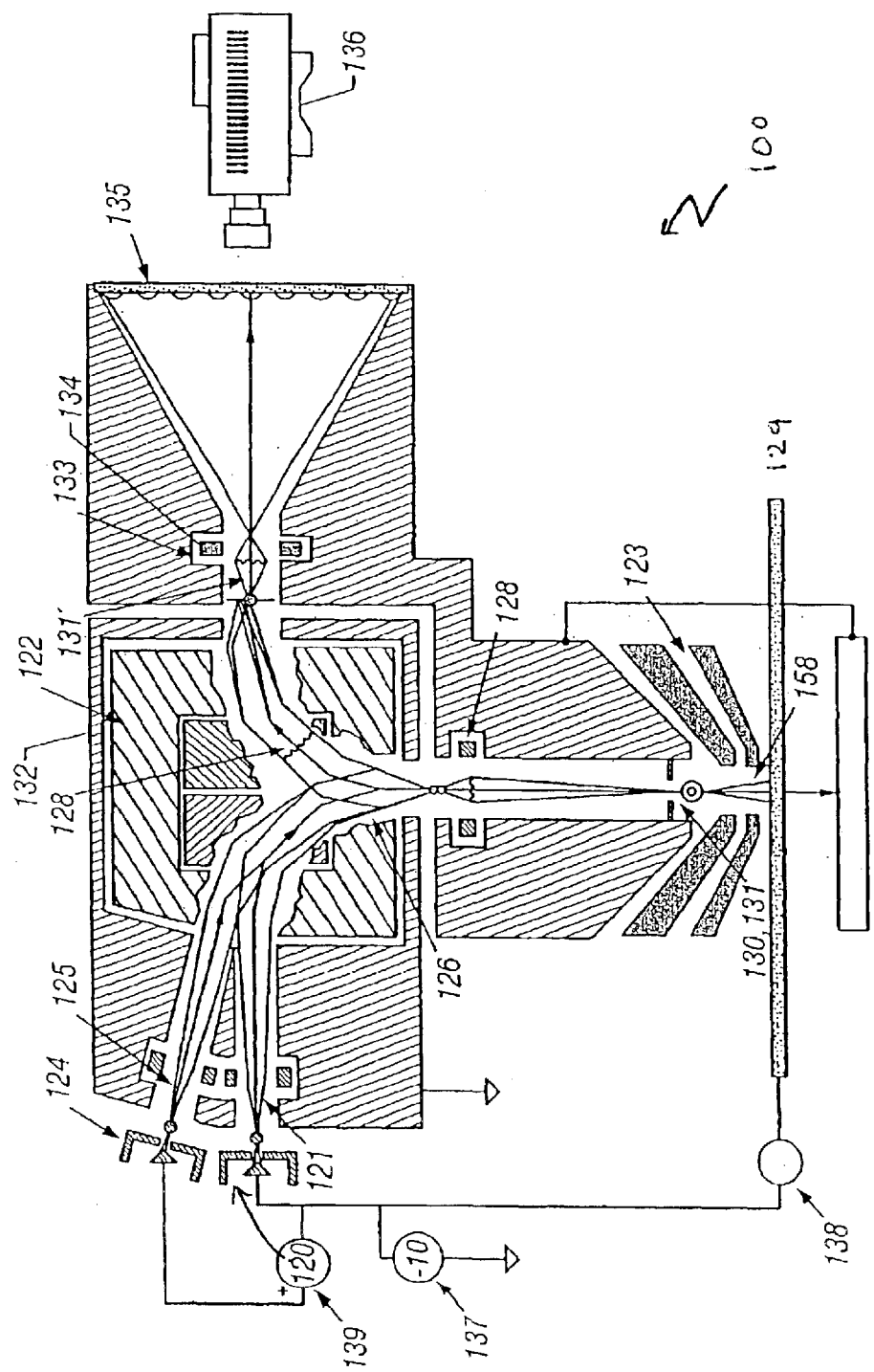
FIG. 1 is a diagram depicting a structure for a prior e-beam apparatus having two illuminating beams.

FIG. 1 is a diagram depicting a structure for a prior e-beam apparatus 100 having two illuminating beams. This prior apparatus 100 is described in International Publication Number WO 01/88514 A1, "Apparatus for Inspection of Semiconductor Wafers and Masks Using a Low Energy Electron Microscope with Two Illuminating Beams," applicant KLA-Tencor Corporation, inventors Lee Veneklasen, David L. Adler, and Matthew Marcus, published Nov. 22, 2001.

In this prior apparatus 100, a first electron gun 120 generates a low energy beam 121, and a second electron gun 124 generates a higher energy beam 125. The electron gun 120 for the low energy beam 121 inserts this beam into the illumination portion of a magnetic separator 122, where it is bent into the axis of the cathode (objective) lens 123. The second gun 124 is located slightly above and behind the low energy gun 120. Since its energy is somewhat higher, the beam 125 from the second gun 124 is bent through a smaller angle in the separator 122, allowing the two beam paths 126 to be superimposed where they enter the cathode lens 123. Either by accurate positioning, or with the help of auxiliary condenser lenses 128, the crossovers from both guns are imaged at their appropriate places 130 and 131 within the cathode lens 123. Within the cathode lens 123, the two beams are decelerated and collimated to form coincident and parallel flood beams 158 that illuminate the substrate 129.

Higher energy backscattered and secondary electrons, along with low energy reflected electrons, are re-accelerated and focused in the cathode lens 123, passing back upwards through the imaging portion of the magnetic separator 122, where they are bent 128 into the axis of the imaging system.

Figure 2:
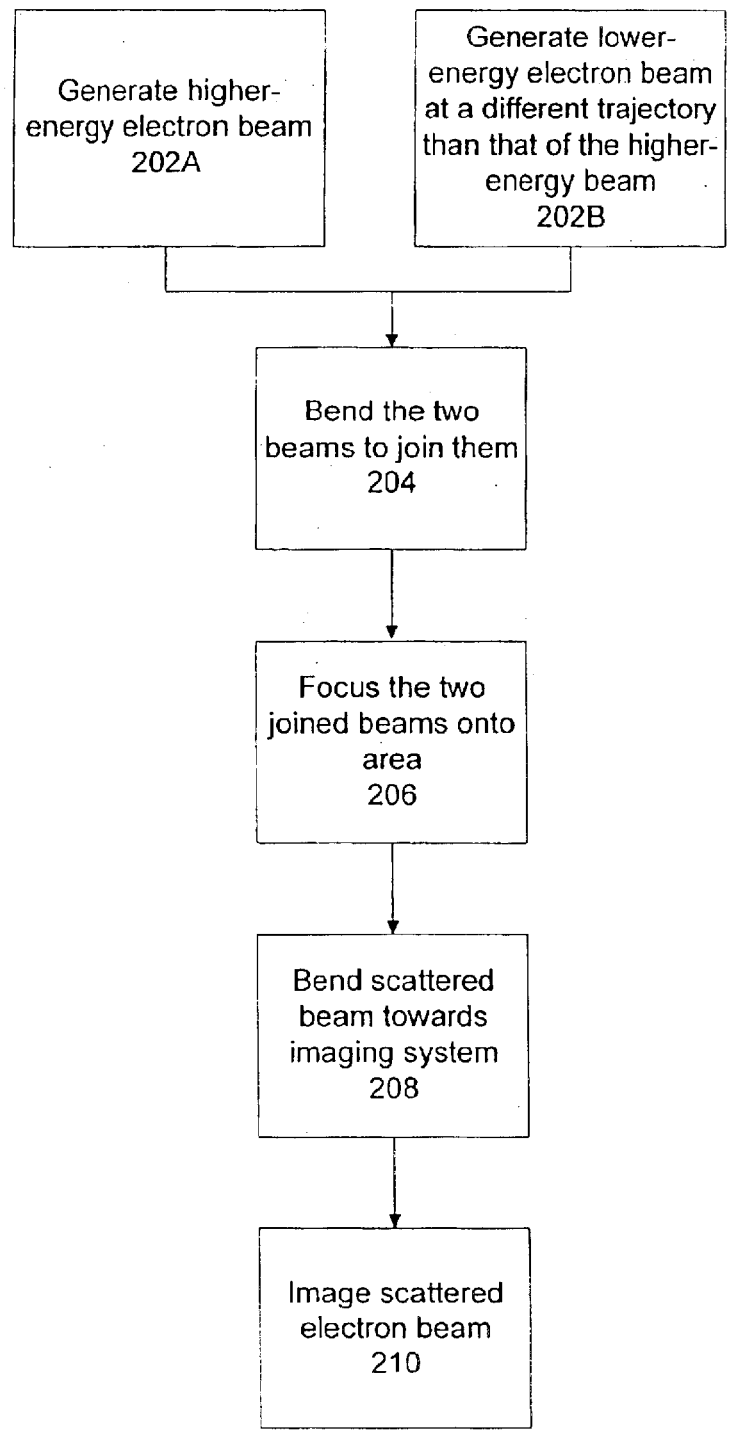
FIG. 2 is a flow chart depicting a prior method for in-line inspection of a substrate using two illuminating beams.

FIG. 2 is a flow chart depicting a prior method 200 for in-line inspection of a substrate using two illuminating beams. A higher-energy e-beam is generated 202A by a first electron gun. Separately, a low-energy beam is generated 202B by a different gun at a different trajectory. The two beams are bent 204 to join them. This is done by a magnetic separator bending the higher-energy beam at less of an angle in comparison to its bending of the low-energy beam. As such, the two beams can be made to be superimposed upon each other. Using the cathode lens(es), the beams are focused 206 (and decelerated and collimated) onto an area of the substrate.

Scattered electrons generated by the impingement of the beams onto the area are directed (i.e. bent) 208 by the magnetic separator to separate them from the low and higher energy electron beams. The scattered beam is bent away from the illumination system and instead towards the projection system. The separation occurs because, within the separator, the scattered electrons have velocity vectors away from the substrate, while the incident electrons have velocity vectors towards the substrate. Finally, the scattered electron beam is imaged 210 to view the illuminated area.

As describe above, the prior apparatus 100 and method 200 use two co-planar guns of different beam energies and inclined beam axes. The guns are configured such that the angle of inclination is equal to the difference in deflection angles caused by the magnetic prism separator. However, this prior technique is disadvantageous in some aspects. For example, it requires biasing of the magnetic prism separator at high voltage in order to achieve sufficient angular separation of the low and high energy beams. This complicates the design and increases the likelihood of high-voltage arcing. Further, the two electron guns must be implemented in close proximity to each other, which makes the design more difficult to implement. The new method and apparatus described below overcomes these disadvantages.

Figure 3:
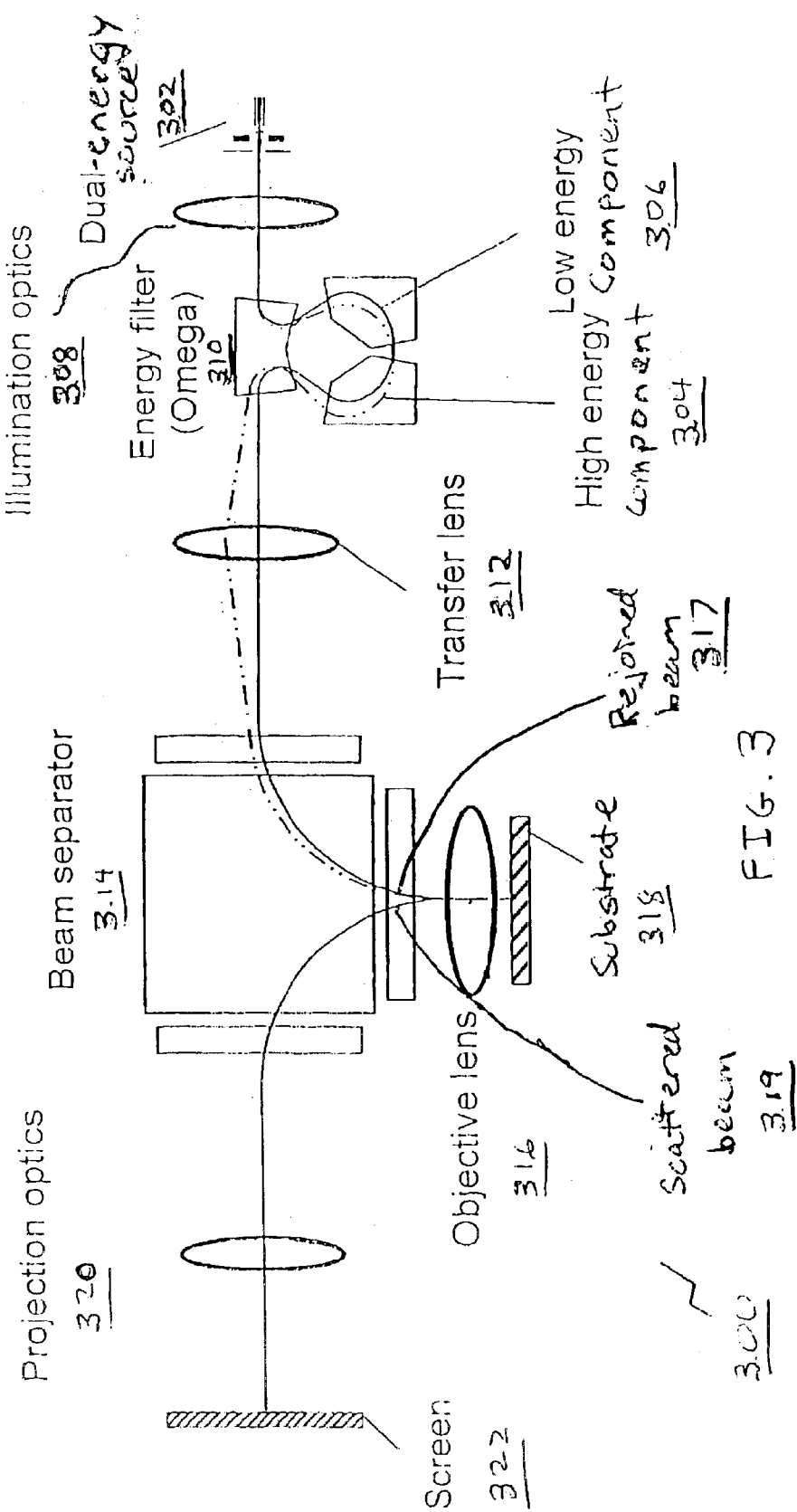
FIG. 3 is a diagram depicting a structure for an electron beam apparatus having two illuminating beams in accordance with an embodiment of the invention.

FIG. 3 is a diagram depicting a structure for an electron beam apparatus having two illuminating beams in accordance with an embodiment of the invention. This apparatus 300 overcomes disadvantages of the prior apparatus described above.

As shown in FIG. 3, the apparatus 300 includes a dual-energy electron source 302. This dual-energy e-beam source 302 may comprise a dual-energy electron gun that is configured to generate both a higher-energy e-beam component 304 and a lower-energy e-beam component 306. In one implementation, the dual-energy e-beam source 302 is composed of two concentric cathodes, an inner disc and an outer annulus. The inner disc may be biased at a high negative voltage with respect to the substrate, while the outer annulus may be biased by an additional negative voltage with respect to the inner disc. For example, the outer annulus may be biased at several hundred volts more negative than the inner disc.

The dual-energy beam is received by illumination optics 308. After the illumination optics, the dual-energy beam enters an energy filter 310. The energy filter 310 operates as an energy-dependent dispersive device. For example, the energy filter may comprise an omega (magnetic) type energy filter. Alternatively, it may comprise an alpha (magnetic) type energy filter. The energy filter 310 introduces dispersion between the lower energy and higher energy components of the e-beam, such that the two e-beam components exit the filter 310 at different angles of trajectory. As illustrated, the higher-energy component 304 may exit the filter 310 inclined at an angle to the optical axis while the lower-energy component 306 exits the filter 310 along the optical axis. In one implementation, the asymptotic object plane of the energy filter 310 is located at the exit plane of the illumination optics 308, and the energy filter 310 forms an asymptotic image that is then transferred into the object plane of the beam separator 314 using a transfer lens 312. The energy filter 310 may, for example, be configured to be operated in a unity magnification mode for ease of implementation.

The beam separator 314 is configured to receive the two dispersed e-beam components and bend the trajectories of the components. The trajectories are bent so as to substantially cancel the dispersion previously introduced by the energy filter 310. As a result, the two e-beam components are rejoined in trajectory as they exit the beam separator 314 and enter the objective lens 316 coaxially.

Because the dispersion previously introduced between the two components is relatively small, less deflection is needed within the beam separator 314 to converge the two components. In comparison, due to the use of two separate guns, greater deflection is needed within the beam separator 122 of the prior apparatus 100. Hence, in accordance with an embodiment of the invention, the beam separator 314 may comprise a more conventional magnetic prism array. For example, the beam separator 314 may be implemented as a compact, double-focusing magnetic prism array that generates uniform magnetic fields of different strength and lengths using grounded pole pieces and without high voltages. Such a magnetic prism array may be advantageously configured to behave as a round lens and enable stigmatic focusing to be used. This substantially simplifies set-up, alignment, and operation of the apparatus.

The objective lens 316 is configured to focus the rejoined beam 317 onto an area of the substrate 318. For example, the substrate 318 may comprise a semiconductor wafer being inspected. The substrate 318 may be electrically floated at approximately the same voltage as one of the cathodes of the source 302, such that the illuminating electrons are decelerated prior to impinging upon the substrate 318.

When the substrate surface is biased slightly more positive than the lower-energy source cathode, impingement of each of the two e-beam components onto the area of the substrate 318 generates a scattered beam 319. The beam 319 includes reflected electrons from the low energy beam 306 and secondary and backscattered electrons generated by the higher energy beam 304. The low energy beam 304 charges the surface negatively, while the high energy beam 304 charges the sample positively, resulting in dynamic charge equilibrium at the surface. The beam 319, containing both the low energy reflected mirror electrons as well as higher energy secondary and backscattered electrons, can be advantageously utilized for imaging in two embodiments.

In one embodiment, electrons generated by the higher-energy component 304 are utilized for imaging, and reflected electrons of the lower-energy component 306 are removed by an aperture. As such, impingement of electrons of the higher-energy component 306 onto the substrate 318 results in a secondary imaging mode where secondary or backscattered electrons make up the scattered beam 319. Such a imaging mode result in images displaying high materials contrast.

In an alternate embodiment, the reflected electrons of the lower-energy component 306 are utilized for imaging, while the higher-energy component 304 is removed by an aperture. As such, impingement of electrons of the lower-energy component 206 onto the substrate 318 results in a mirror imaging mode where reflected electrons make up the scattered beam 319. Such a mirror imaging mode result in intense, high contrast images of substrate topography. The electrons of the scattered beam 319 (whether composed of backscattered, secondary, or reflected electrons) are accelerated and focused by the objective lens 316. The scattered beam 319 passes back upwards through the beam separator 314. The beam separator 314 is configured to separate the scattered beam 319 from the incident (rejoined) beam 317 by bending the scattered beam 319 towards the axis of the projection optics 320. The projection optics 320 is configured to image the scattered e-beam 319 onto a screen (or array of detectors) 322.

Figure 4:
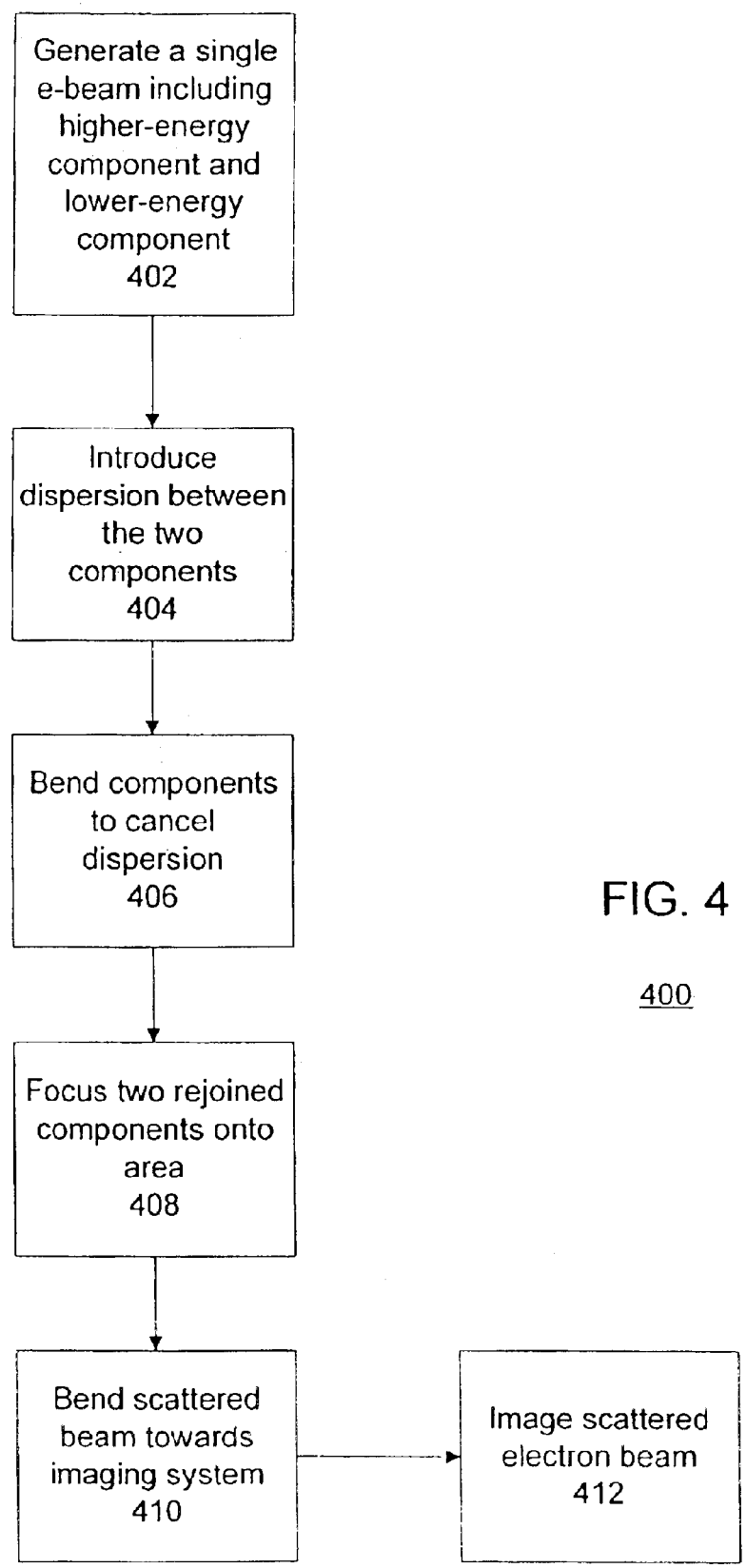
FIG. 4 is a flow chart depicting a method for in-line inspection of a substrate using two illuminating beams in accordance with an embodiment of the invention.

FIG. 4 is a flow chart depicting a method for in-line inspection of a substrate using two illuminating beams in accordance with an embodiment of the invention. This method 400 overcomes disadvantages of the prior method described above.

A single dual-energy e-beam is generated 402 by a dual-energy electron gun. Dual-energy e-beam includes a higher-energy e-beam component and a lower-energy e-beam component. Both components have the same coaxial trajectory so that they make up a single beam.

Dispersion is then introduced 404 between the two beam components. The dispersion may be introduced by, for example, an energy filter. The two components enter the energy filter along the same trajectory, but they leave the energy filter with different angles of trajectory.

The two dispersed components are bent 406 to substantially cancel out the dispersion and rejoin the components into a single beam. This may be done by a beam separator bending the higher-energy beam at slightly less of an angle in comparison to its bending of the low-energy beam. As such, the two components can be rejoined coaxially (i.e. once again be superimposed upon each other). Using the objective lens, the single beam (with two rejoined components) is focused 408 (and decelerated and collimated) onto an area of the substrate.

Impingement of the rejoined e-beam components onto the substrate area generates scattered electrons. In one embodiment, impingement of the higher-energy component onto the area generates secondary electrons (approximately 1 to 30 eV landing energy) and/or backscattered electrons (approximately 30 to few 100 eV landing energy), and impingement of the lower-energy component provides electrons to compensate for unwanted surface charging. In an alternate embodiment, impingement of electrons of the lower-energy component onto the area generates reflected electrons, and electrons of the higher-energy component are utilized to supply some positive surface charging by ejecting electrons with a yield greater than unity.

The scattered electrons (whether backscattered electrons, secondary electrons, or reflected electrons) are deflected (i.e. bent) 410 by the beam separator to separate them from the low and higher energy illumination electron beams. The scattered beam is deflected away from the illumination system and instead towards the projection system. The separation occurs because, within the separator, the scattered electrons have velocity vectors away from the substrate, while the incident electrons have velocity vectors towards the substrate. Finally, the scattered electron beam is imaged 412 to view the illuminated area. The image data may be used, for example, for inspecting a semiconductor wafer.

The new apparatus and method described above overcomes disadvantages of the prior apparatus and method. The new design allows for use of a conventional prism design (without the need for high voltages) because the two e-beam components are only slightly dispersed and so relatively easy to rejoin. In comparison, the prior design required a non-conventional prism design with high voltages needed to converge the two separate beams. Hence, the risk of arcing within the prism is avoided.

Further, a single dual-energy gun is used in the new design, instead of two guns in close proximity in the prior design. This simplifies the electron source portion of the apparatus and makes the new design easier to implement.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An apparatus for inspection of substrates, the apparatus comprising:

a dual-energy electron beam (e-beam) source configured to generate both a higher-energy e-beam component and a lower-energy e-beam component;

an energy-dependent dispersive device configured to introduce dispersion between said two e-beam components, wherein said two e-beam components exit the dispersive device at different angles of trajectory;

a beam separator configured to receive said two dispersed e-beam components and substantially cancel said dispersion so that said two e-beam components are rejoined in trajectory; and an objective lens configured to focus said two rejoined e-beam components onto an area of the substrate.

2. The apparatus of claim 1, wherein impingement of one component of the two e-beam components onto the area generates a scattered e-beam that is utilized for imaging, and wherein impingement of both the components of said e-beam onto the area provides compensation for surface charging.

3. The apparatus of claim 2, wherein said one component comprises the higher-energy e-beam component, and wherein secondary or backscattered electrons are utilized for imaging.

4. The apparatus of claim 3, wherein the scattered e-beam comprises backscattered electrons.

5. The apparatus of claim 3, wherein the scattered e-beam comprises secondary electrons.

6. The apparatus of claim 2, wherein said one component comprises the lower-energy e-beam component, and wherein the scattered e-beam comprises reflected electrons.

7. The apparatus of claim 1, wherein the dual-energy e-beam source comprises two concentric cathodes.

8. The apparatus of claim 4, wherein the two concentric cathodes comprise an inner cathode biased at a high negative voltage with respect to the substrate, and an outer cathode biased by an additional negative voltage with respect to the inner cathode.

9. The apparatus of claim 1, wherein the energy-dependent dispersive device is operated in a unity magnification mode.

10. The apparatus of claim 1, wherein the energy-dependent dispersive device comprises an omega type energy filter that disperses said two e-beam components using magnetic fields.

11. The apparatus of claim 1, wherein the energy-dependent dispersive device comprises an alpha type energy filter that disperses said two e-beam components using magnetic fields.

12. The apparatus of claim 2, wherein the beam separator is further configured to separate the scattered e-beam from said two e-beam components.

13. The apparatus of claim 2, further comprising: projection optics configured to image the scattered e-beam.

14. The apparatus of claim 1, further comprising:
a transfer lens configured to transfer said two dispersed e-beam components from the energy-dependent dispersive device to the beam separator.

15. A method for in-line inspection of a substrate, the method comprising:
generating dual-energy e-beam including a higher-energy e-beam component and a lower-energy e-beam component;
introducing dispersion between said two e-beam components so that said two e-beam components have different angles of trajectory;
substantially canceling said dispersion so that said two e-beam components are rejoined in trajectory; and
focusing said two rejoined e-beam components onto an area of the substrate.

16. The method of claim 15,
wherein impingement of one component of the two e-beam components onto the area generates a scattered e-beam, and
wherein impingement of both components of said e-beam onto the area provides compensation for surface charging.

17. The method of claim 16,
wherein said one component comprises the higher-energy e-beam component, and
wherein secondary or backscattered electrons are utilized for imaging.

18. The method of claim 17, wherein the scattered e-beam comprises backscattered electrons.

19. The method of claim 17, wherein the scattered e-beam comprises secondary electrons.

20. The method of claim 16,
wherein said one component comprises the lower-energy e-beam component, and
wherein the scattered e-beam comprises reflected electrons.

21. The method of claim 16, further comprising:
separating the scattered e-beam from said two e-beam components.

22. The method of claim 16, further comprising:
imaging the scattered electron beam so as to provide image data by which to inspect the substrate.

23. An apparatus for in-line inspection of a substrate, the apparatus comprising:
means for generating dual-energy e-beam including a higher-energy e-beam component and a lower-energy e-beam component;
means for introducing dispersion between said two e-beam components so that said two e-beam components have different angles of trajectory;
means for substantially canceling said dispersion so that said two e-beam components are rejoined in trajectory; and
means for focusing said two rejoined e-beam components onto an area of the substrate.

* * * * *